United States Patent
Hanna et al.

(10) Patent No.: US 6,363,269 B1
(45) Date of Patent: Mar. 26, 2002

(54) SYNCHRONIZED MODULATION/DEMODULATION METHOD AND APPARATUS FOR FREQUENCY DIVISION MULTIPLEXED SPECTROPHOTOMETRIC SYSTEM

(75) Inventors: D. Alan Hanna; Mark A. Norris, both of Boulder, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/465,304

(22) Filed: Dec. 17, 1999

(51) Int. Cl.[7] .................................................. A61B 5/00
(52) U.S. Cl. ...................................... 600/322; 600/336
(58) Field of Search ................ 600/309–311, 322–324, 600/336, 315–316, 326, 328, 330; 356/39–41

(56) References Cited

U.S. PATENT DOCUMENTS

| | | | |
|---|---|---|---|
| 4,603,700 A | | 8/1986 | Nichols et al. |
| 4,800,885 A | | 1/1989 | Johnson |
| 4,807,630 A | * | 2/1989 | Malinouskas ............... 600/323 |
| 4,832,484 A | | 5/1989 | Aoyagi et al. ................ 356/41 |
| 4,848,901 A | * | 7/1989 | Hood, Jr. ..................... 356/41 |
| 5,279,295 A | * | 1/1994 | Martens et al. ............. 600/335 |
| 5,337,745 A | | 8/1994 | Benaron |
| 5,343,818 A | | 9/1994 | McCarthy et al. |
| 5,503,148 A | | 4/1996 | Pologe et al. |
| 5,685,301 A | | 11/1997 | Klomhaus |
| 5,685,308 A | * | 11/1997 | Wright et al. ............... 600/443 |
| 5,720,284 A | | 2/1998 | Aoyagi et al. |
| 5,722,398 A | | 3/1998 | Ishihara et al. |
| 5,766,125 A | | 6/1998 | Aoyagi et al. ............... 600/310 |
| 5,766,127 A | | 6/1998 | Pologe et al. ............... 600/310 |
| 5,779,630 A | | 7/1998 | Fein et al. ................... 600/323 |
| 5,782,758 A | | 7/1998 | Ausec et al. ................ 600/336 |
| 5,800,348 A | | 9/1998 | Kaestle ........................ 600/322 |
| 5,842,979 A | | 12/1998 | Jarman ........................ 600/322 |
| 5,891,022 A | | 4/1999 | Pologe ........................ 600/323 |
| 5,919,134 A | | 7/1999 | Diab ........................... 600/323 |
| 5,954,644 A | | 9/1999 | Dettling et al. ............. 600/322 |
| 5,995,858 A | * | 11/1999 | Kinast ......................... 600/323 |
| 6,018,674 A | | 1/2000 | Aronow ...................... 600/322 |

* cited by examiner

*Primary Examiner*—Eric F. Winakur
*Assistant Examiner*—Matthew Kremer
(74) *Attorney, Agent, or Firm*—Marsh Fischmann & Breyfogle LLP

(57) ABSTRACT

An improved method and apparatus is disclosed for use in frequency division multiplexed spectrophotometric systems. In photoplethysmographic applications the invention provides for the modulation of a plurality of light sources at different frequencies and in accordance with a predetermined phase relationship. Light from the sources that is transmitted through a tissue under test is detected at a detector. A composite signal indicative of the intensity of light received at the detector is demodulated based on the different modulation frequencies and predetermined phase relationship to obtain signal portions corresponding with each of the light sources. Modulation and demodulation are synchronized during each measurement period. The modulation waveforms used to modulate the light sources and corresponding demodulation waveforms used to demultiplex the composite signal are symmetrically timed about a center point for each of the measurement periods. The invention reduces artifacts associated with rising/falling light source amplitude levels, thereby reducing system noise sensitivity.

15 Claims, 2 Drawing Sheets

SYNCHRONIZED MODULATION/ DEMODULATION METHOD AND APPARATUS FOR FREQUENCY DIVISION MULTIPLEXED SPECTROPHOTOMETRIC SYSTEM

FIELD OF THE INVENTION

The present invention relates to spectrophotometric analysis for measuring the concentrations of a plurality of analytes in a given sample, and more particularly, to the use of frequency division multiplexed signals in such analysis. The invention is particular apt for use in photoplethysmographic systems, and even more specifically, in pulse oximetry applications.

BACKGROUND OF THE INVENTION

Spectrophotometric analysis is employed to estimate the concentration of one or more analytes in a given sample and entails the passage of light from one or more light source(s) through the sample. The amount of light transmitted through the sample is measured and typically employed in one or more calibration equation(s) to obtain the analyte concentration estimate(s). The calibration equation(s) is based upon the unique light absorption characteristics of each analyte(s) to be measured.

In the field of photoplethysmography, pulses of light having different center wavelengths are transmitted through a tissue under test to non-invasively determine various blood analyte values. More particularly, pulse oximeters are employed to determine pulse rates and blood oxygen levels, and typically include a probe that is releasably attached to a patient's appendage (e.g., finger, ear lobe or nasal septum). The probe directs light signal pulses generated by a plurality of emitters through the appendage, wherein portions of the light signals are absorbed by the tissue. The intensity of light transmitted by the tissue is monitored by one or more detector(s) which outputs a signal(s) indicative of the light absorbency characteristics of the tissue. Because the blood analytes of interest absorb more light at one wavelength than at another wavelength, the detector output signal(s) may be used to compute the blood analyte concentrations.

By way of primary example, it is known that oxyhemoglobin (O2Hb) absorbs light more readily in the infrared region than in the red region, whereas reduced hemoglobin (RHb), or deoxyhemoglobin, more readily absorbs light in the red region than in the infrared region. As such, oxygenated blood with a high concentration of oxyhemoglobin and a low concentration of reduced hemoglobin will tend to have a high ratio of optical transmissivity in the red region to optical transmissivity in the infrared region. The relative transmissivity of blood at red and infrared center wavelengths may be employed as a measure of blood oxygen saturation (SpO2). See, e.g., U.S. Pat. No. 5,503,148, hereby incorporated by reference in its entirety.

It is also recognized that concentrations of other related blood constituents (e.g., carboxyhemoglobin (COHb) and methemoglobin(MetHb)) can be measured with a similar approach since such analytes also have unique light absorbency characteristics at different corresponding center wavelengths. The determination of such additional constituents can serve to enhance the measurement of blood oxygen saturation. See, e.g., U.S. Pat. No. 5,842,979, hereby incorporated by reference it its entirety.

In pulse oximetry applications where a single detector is used, some modulation method must be employed with the different light sources so that tissue light transmission corresponding with each of the sources can be distinguished in the multiplexed detector output signal. One approach, called time-division multiplexing, provides for the pulsing of the light sources at different predetermined or monitored points in time during the modulation cycle so that the multiplexed detector output signal can be demultiplexed based on the monitored transmission times. See., e.g., U.S. Pat. No. 5,954,644, hereby incorporated by reference in its entirety. In frequency-division multiplexing approaches, the different light sources are pulsed at different frequencies so that the frequency of pulsing becomes the basis for demultiplexing the multiplexed detector output signal. That is, the detector output signal may be demodulated at each of the frequencies used to modulate the light sources so as to separate signal portions corresponding with each of the light sources. See, e.g., U.S. Pat. No. 4,800,885, hereby incorporated by reference in its entirety.

As will be appreciated, the detector output signal in pulse oximeters contains non-pulsatile and pulsatile components. The non-pulsatile component is influenced by the absorbency of tissue, venous blood, capillary blood, non-pulsatile arterial blood, the intensity of the light signals and the sensitivity of the detector. The pulsatile component reflects the expansion of the arteriolar bed with arterial blood. The varying amplitude of the pulsatile component depends upon the blood volume change per pulse and the oxygen saturation level of the blood. As such, the pulsatile component provides a basis for monitoring changes in the concentration of the noted blood analytes.

Given the relatively small contribution of the pulsatile component to the output signal of a detector in pulse oximeters, it has been recognized that the quality of analyte and oxygen saturation measurements can be significantly impacted by the presence of system noise. In this regard, any phenomena, whether mechanical, electrical or optical, that causes an artifact in the pulsatile component of a detector output signal can significantly compromise performance. Of primary interest here are artifacts that can arise due to rising/falling light amplitude levels associated with ambient light changes or due to electrical interference.

SUMMARY OF THE INVENTION

A broad objective of the present invention is to provide a spectrophotometric system having improved reliability.

More particularly, a primary objective of the present invention is to provide a photoplethysmographic method and apparatus yielding improved reliability through the reduction of system noise sensitivity. Relatedly, an objective of the present invention is to attenuate artifacts occasioned by rising/falling ambient light signal amplitudes, and by electrical interference.

The above objectives and additional advantages are realized in an inventive photoplethysmographic measurement apparatus that includes a plurality of light sources for emitting light signals at different corresponding wavelengths into a tissue under test and a detector for detecting at least a portion of the light signals transmitted through the tissue under test. Modulation means are included for modulating the light signals at corresponding different carrier frequencies and in accordance with a predetermined phase relationship therebetween. Correspondingly, demodulation means are included for demodulating a composite detection signal (e.g., a multiplexed signal corresponding with an output signal from the detector that indicates the intensity of the detected light signals), based upon the different carrier frequencies and in accordance with the predetermined phase relationship, to obtain signal portions corresponding with each of the light sources. In turn, such signal portions are employable to determine a blood analyte level in the tissue under test.

Of note, the inventive apparatus may include a synchronization means for synchronizing operation of the modulation means and demodulation means during each of one or more analyte measurement periods. In one arrangement, such synchronization means may comprise a master clock for providing clocking signals to the modulation means and demodulation means as embodied in a digital signal processor. As will be appreciated upon further consideration, enhanced measurement reliability may be realized via the maintenance of both a predetermined phase relationship between the modulated light signals and synchronization of the modulation and demodulation processes.

The noted modulation means may define a plurality of different periodic waveforms for modulating a corresponding plurality of light sources, and similarly the referenced demodulation means may define a common plurality of corresponding demodulation waveforms for demodulating the composite detection signal to obtain a plurality of signal portions that correspond with the plurality of light sources. In this regard, the modulation waveform/demodulation waveform set corresponding with each given light source should be orthogonal to the modulation/demodulation waveform sets corresponding with the other light sources. To establish an orthogonal relationship, the modulation and demodulation waveforms should preferably be of a type(s) selected from a group consisting of: sinusoidal waveforms, square waveforms and their combinations.

Further, the modulation and demodulation waveforms corresponding with each given light source should be provided to complete an equal, predetermined, integer number of cycles during each measurement period, and each different modulation/demodulation waveform set should be provided to complete a different integer number of cycles for each of the measurement periods. For example, first modulation/demodulation waveforms corresponding with a first light emitter may be precisely defined by a digital processor to complete two cycles during each measurement period, and second modulation/demodulation waveform corresponding with a second light emitter may be precisely defined by a digital processor to complete three cycles during each measurement period. Obviously, other integer ratios may also be employed. The use of precise, or exact, synchronized integer ratios between different modulating frequencies and the measurement period greatly reduces crosstalk between channels.

In a related aspect of the present invention, the modulation waveforms applied to the light sources and the demodulation waveforms used for processing the composite detector signal should be synchronized so as to be symmetrically timed about a center point of each measurement period. That is, each of such waveforms should be provided so that symmetric halves are defined about the center point of each measurement period (e.g., an even function such as cosine). This reduces system sensitivity to the effects of the frequency drift.

Further, and in yet another related aspect of the invention, the composite detection signal may comprise a plurality of measurement values obtained via a sampling means (e.g., sampling of a detector output signal by an analog to digital convertor/digital processor arrangement) at a predetermined rate which is at least 2 times the rate of the greatest modulation frequency applied to any of the light sources (i.e., the Nyquist limit). Even more preferably, the predetermined sampling rate may be at least 5 times the greatest modulation frequency. Such an approach provides for the obtainment of a plurality of measurement values during each cycle of all demodulation waveforms. In turn, the measurement values may be separately employed with each of the demodulation waveforms to obtain the signal portions corresponding with each of the light sources.

For example, for each given demodulation waveform, each of the measurement values obtained for a measurement period may be multiplied by a corresponding-in-time value extracted from the demodulation waveform (e.g., a relative value between +1 and −1), and the products may be summed or low pass filtered and decimated to yield a demodulated signal portion value. The signal portion value is indicative of the amount of light absorption by the tissue under test at the wavelength of the corresponding light source. As such, the extracted signal portion values corresponding with the plurality of light sources may be employed to determine the desired blood analyte levels (e.g., concentration values for oxygenated hemoglobin, and reduced hemoglobin where 2 light sources and 2 corresponding modulation/demodulation waveforms are utilized; and concentration values for oxygenated hemoglobin reduced hemoglobin, carboxyhemoglobin and methemoglobin where 4 light sources and 4 corresponding modulation/demodulation waveforms are employed).

Based upon the foregoing, it should be appreciated that the present invention also provides a general method for use in photoplethysmographic measurement systems having a plurality of pulsed light sources for illuminating a tissue under test and a detector for receiving a portion of the light pulses transmitted by the tissue under test. Such method includes the steps of modulating each of the plurality of light sources at different pulsing frequencies and in accordance with a predetermined phase relationship therebetween, and demodulating a composite detection signal based on the different pulsing frequencies and predetermined phase relationship. The composite detection signal is indicative of the intensity of the portion of the light pulses received by the detector, and may comprise or be derived from a detector output signal. The modulating and demodulating steps corresponding with each given one of the plurality of pulsing frequencies may be synchronized during each of one or more analyte measurement periods. Demodulation of the composite detection signal yields signal portions corresponding with each of the light sources that may be utilized for blood analyte measurement.

The inventive method may further include the step of defining a plurality of different modulation waveforms for use in the modulating step and a corresponding plurality of different demodulation waveforms for use in the demodulating step. Such modulation and demodulation waveforms should be periodic in nature and symmetrically timed about the center point of each given measurement period. Further in this regard, the defining step may be provided so that modulation and demodulation waveforms corresponding with each of the light sources are orthogonal to the modulation and demodulation waveforms corresponding with all other light sources as described above.

In another aspect of the inventive method, the composite signal may comprise a plurality of different measurement values which are obtained via a sampling step. Such sampling step may comprise a sampling of a detector output signal (or signal derived therefrom) at a predetermined rate which is at least 2 times the rate of the greatest modulation frequency applied to any of the light sources. Even more preferably, the predetermined sampling rate may be at least 5 times the greatest modulation frequency. The inventive method may also include a step of using the measurement values together with each of the demodulation waveforms to obtain the signal portions for each given demodulation waveform. For example, for each demodulation waveform, each of the measurement values obtained for a measurement period may be multiplied by a corresponding-in-time value extracted from the demodulation waveform, and the products may be summed for the measurement period to yield a demodulated signal portion value. As will be appreciated, the extracted signal portion values corresponding with each of the light sources may be employed to determine the desired blood analyte levels.

In view of the foregoing summary of the inventive apparatus and method, a number of advantages will be apparent to those skilled in the art. In particular, the system provides for significant attenuation of artifacts caused by electromagnetic interference. Additionally, the system is relatively insensitive to the effects of ambient light and even to the effects of flickering ambient light (such as that produced by fluorescent lamps and computer monitor screens), provided that the modulation/demodulation waveform frequencies are chosen so as to avoid the characteristic harmonics of these devices. Further, the sampling of a composite detection signal at a rate of at least 2 times the greatest modulation/demodulation frequency, followed by the combinative use of the multiple values in the demodulation process, tends to reduce quantization noise. This allows the use of A/D converters of lower precision.

Numerous additional aspects and advantages of the present invention will become apparent to those skilled in the art based upon further consideration of the description that follows.

DETAILED DESCRIPTION

Figure 1:
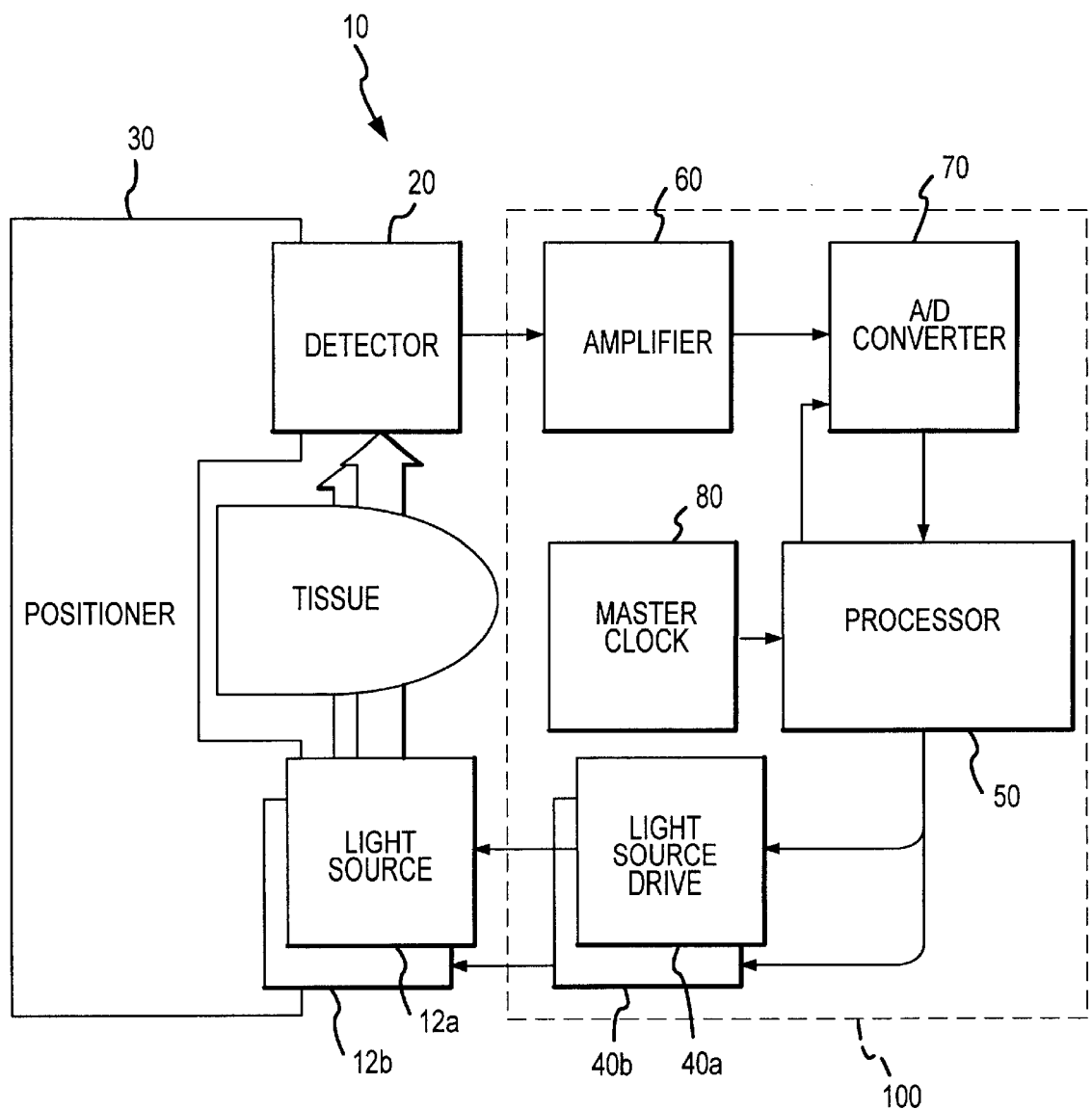
FIG. 1 illustrates a block diagram of a system architecture for one embodiment of the present invention.

FIG. 1 illustrates one embodiment of a system architecture for the present invention. The pulse oximeter system 10 comprises aplurality of light sources 12a, 12b (e.g., light emitting diodes (LEDs) or laser diodes) for emitting light signals at different center wavelengths through a tissue under test and on to a photodetector 20 (e.g., photosensitive diode). A positioner 30, or probe, is provided to align the light signals with detector 20. By way of example, positioner 30 may be of a clip-type or flexible strip configuration adapted for selective attachment to a patient's appendage (e.g. finger).

Additional components of system 10 may be housed in a monitor 100. More particularly, such components may include light source drives 40a, 40b, corresponding with the light sources 12a, 12b. The drive signals provided by light source drives 40a, 40b contemporaneously activate light sources 12a, 12b to emit light pulses at different frequencies.

In the later regard, monitor 100 may further comprise a digital processor 50 preprogrammed to define modulation waveforms, or drive patterns, for each of the light sources 12a, 12b, in accordance with predetermined values obtained from a look-up table. More particularly, digital processor 50 may provide separate digital output trigger signals to the light source drives 40a, 40b, which in turn provide separate analog drive output signals to the light sources 12a, 12b to achieve the desired pulsing frequencies. It should be noted that while the illustrated embodiment indicates that the light sources 12a, 12b are physically interconnected to the positioning device 30 (e.g., via mounting within the positioning device 30 or via mounting within a connector end of a cable selectively connectable to the positioning device 30), light sources 12a, 12b may alternately be disposed in monitor 100 with optical fiber interconnects through a connecting cable to the positioning device 30.

As shown in FIG. 1, the composite output signal from detector 30 is provided to an amplifier 60 that converts the analog current signal into a voltage signal. The detector output signal reflects the intensity of the light pulses from sources 12a, 12b transmitted through the tissue under test and received at detector 20. The amplifier 60 may be further provided to filter the signal so as to remove noise and reduce aliasing. For example, all signal components having frequencies that exceed a predetermined level above the highest light source modulation frequency can be filtered out.

The analog voltage signal output by the amplifier 60 is provided to an analog-to-digital (A/D) converter 70 that converts the voltage signal into a series of digital output sample values representing the intensity of the analog current output from detector 30. The conversion rate of the A/D converter 70 should be sufficient to provide for accurate tracking of the shape of the various signal portions comprising the detector 30 analog current output signal. For example, A/D converter 70 may be provided to accommodate a sampling rate that is at least 2 times, and preferably at least 5 times, the highest light source modulating frequency. See, also U.S. patent application Ser. No. _____, filed Dec. 17, 1999, entitled "OVERSAMPLING PULSE OXIMETER", hereby incorporated by reference in its entirety.

The digital output signal from the A/D converter 70 is provided to the processor 50 which may perform a number of processing functions. In particular, digital processor 50 may be provided with demodulation software to separate signal portions from the composite digital signal that correspond with the transmitted light signals from each of light sources 12a, 12b received at detector 30. More particularly, the composite digital signal components (i.e., the sampled values) may be separately multiplied by corresponding-in-time values extracted from each of the demodulation waveforms (e.g., relative values between +1 and –1) across each given measurement period, and the products may be summed or low pass filtered and decimated to obtain a separate average intensity/measurement period value corresponding with each light source.

Relatedly, processor 50 may be provided with processing software that utilizes the average intensity/measurement period values to calculate concentrations of one or more blood analytes. Such calculations may be conducted using known techniques.

Referring again to FIG. 1, it can be seen that monitor 100 may also house a master clock 80 interconnected to provide clocking signals to processor 50. In turn, processor 50 may provide trigger signals to A/D converter 70. As will be appreciated, master clock 80 may also be directly interconnected to other system components for synchronization purposes. As to processor 50, master clock 80 functions to coordinate, or synchronize, operation of the demodulation software and modulation software resident at processor 50 in accordance with preprogrammed instruction sets. More particularly, master clock 80 functions with digital processor 50 to define predetermined timing and phase relationships between the modulation/demodulation waveforms and measurement periods.

Figure 2:
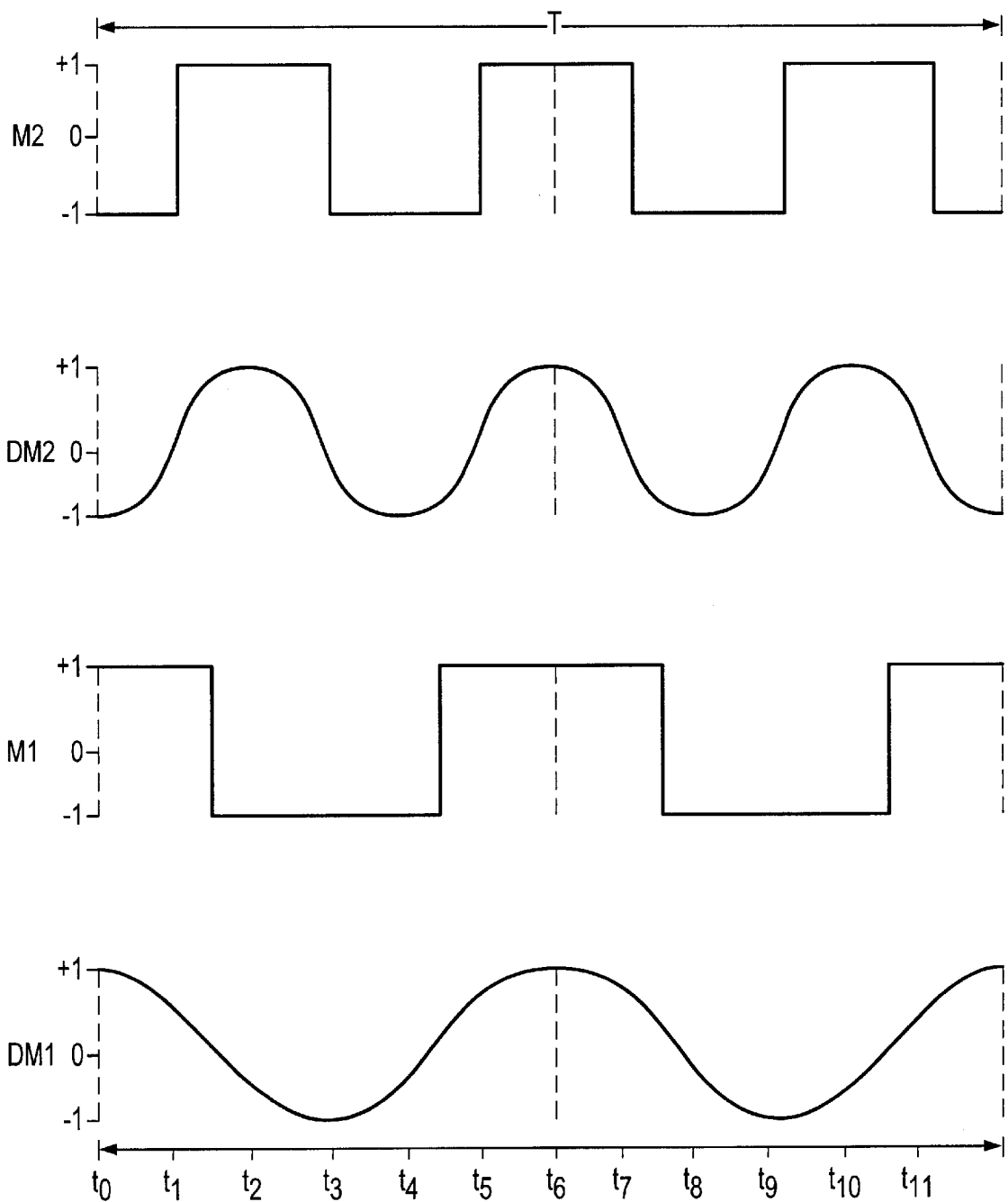
FIG. 2 illustrates a timing diagram for modulation and demodulation waveforms that may be utilized in the embodiment of FIG. 1.

In this regard, reference is now made to FIG. 2. which illustrates a first modulation waveform M1 for use in driving light source 12*a*, a second modulation waveform M2 for use in driving light source 12*b*, a first demodulation waveform DM1 for demodulating the composite detection signal provided by A/D connector 70 to obtain signal portions corresponding with the light signal received from light source 12*a*, and a second demodulation waveform DM2 for demodulating the composite detection signal to obtain signal portions corresponding with the light signal received from light source 12*b*.

As illustrated, each of the waveforms M1, DM1, M2 and DM2 are of a periodic nature and are timed to be symmetrically centered about the center point of an exemplary predetermined measurement time period T. The symmetry of the waveforms about the center point of the measurement period improves the accuracy of the transmitted intensity reading from each light source. Further, it can be seen that waveform M1 is provided to complete two complete integer cycles during a given measurement period T, with the center of the measurement time period T occurring between the two cycles. Waveform M2 is provided to complete three complete cycles during the measurement time period T, with the center of the measurement period defined so that one and one-half cycles of the waveform M2 occurs both prior to and after the center of the measurement period T. Similarly, the demodulation waveforms DM1 and DM2 are provided to complete a corresponding number of cycles in synchronized phase relation to waveforms M1 and M2, respectively. As such, waveforms M1 and M2, as well as waveforms DM1 and DM2, define the same integer ratio therebetween. The fixed phase relationship between M1 and DM1 and between M2 and DM2 provides phase-locked detection, which further increases the discrimination of the system against ambient light interference.

With further reference to FIG. 2, it can be seen that if a sampling rate of the A/D converter 70 is established at 4 times the frequency or modulation rate of waveforms M2 and DM2, then the composite detection signal may comprise data values obtained at times $t_{0 \text{ to } 11}$ during the measurement period. As noted above, such values may be separately multiplied by corresponding-in-time values (i.e., at times $t_{0 \text{ to } 11}$) extracted from each of the demodulation waveforms DM1 and DM2 (e.g., relative values between +1 and −1). Then, the products corresponding with each demodulation "channel" may be summed to yield light intensity measurement values that may be employed to determine the light absorption of the tissue under test at each of the center wavelengths corresponding with sources 12*a*, 12*b*. In turn, the desired analyte levels may be determined.

In one arrangement, light sources 12*a* and 12*b* may be provided to emit light pulses at center wavelengths of approximately 660 nm and 940 nm, respectively, at pulsing frequencies of about 600 hz. and 900 hz., respectively. As will be recognized, such center wavelengths facilitate the measurement of oxyhemoglobin and deoxyhemoglobin concentrations. Further, the system may be provided to define one or more measurement periods, each having a duration of about 1/300 second. In turn, the A/D converter 70 may be provided to sample at a rate of above 1500 hz.

The embodiment described above is for purposes of facilitating an understanding of the present invention and is not intended to limit the scope of the invention in any way. Numerous modifications, adaptions and extensions will be apparent to those skilled in the art.

For example, while the described embodiment is directed to the use of two light sources and two sets of corresponding modulation/demodulation waveforms, it will be appreciated that the present invention may be also readily implemented with a greater number of light sources and corresponding modulation/demodulation waveform sets. In particular, where concentrations of oxyhemoglobin, deoxyhemoglobin, carboxyhemoglobin and methemoglobin are all desired (e.g., as a percentage of total hemoglobin), four different light sources may be utilized having four different center wavelengths (e.g., approximately 660 nm, 940 nm, 640 nm and 800 nm). Further, such light sources may be pulsed at different frequencies (e.g., 500 hz, 600 hz, 700 hz and 800 hz), and four different sets of modulation/demodulation waveforms may be employed, wherein an integer number of cycles for each modulation/demodulation waveform set is defined (e.g., two cycles per measurement period for the first set, three complete cycles per measurement period for the second set, four cycles per measurement period for the third set and five cycles per measurement period for the fourth set).

Additionally, while FIG. 2 shows sinusoidal and square waveforms for DM1, DM2 and M1, M2, respectively, numerous other combinations of periodic waveforms may be employed. For example, any of the modulation and/or demodulation waveforms may be of a type that is sinusoidal, square or combinations thereof.

Such modified embodiments and other like embodiments are intended to be within the scope of the present invention as defined by the claims that follow.

What is claimed is:

1. A photoplethysmographic measurement apparatus for measuring a blood analyte level in a tissue under test, comprising:

a plurality of light sources for emitting a corresponding plurality of light signals at different corresponding wavelengths to said tissue under test;

modulation means for modulating the light signals according to a predefined plurality of different periodic modulation waveforms at corresponding different frequencies and in accordance with a predetermined phase relationship therebetween;

a detector for detecting at least a portion of said light signals transmitted through said tissue under test;

demodulation means for demodulating a composite signal indicative of an intensity of said detected portion of said plurality of light signals according to a predefined plurality of different periodic demodulation waveforms which correspond to said plurality of periodic modulation waveforms, wherein said demodulation is based on said different frequencies and said predetermined phase relationship to obtain signal portions corresponding with each of said light signals, and wherein said signal portions are employable to determine a blood analyte level in said tissue under test; and synchronization means for synchronizing operation of said modulation means and demodulation means during each of one or more measurement periods so that each of said modulation waveforms and demodulation waveforms are symmetrically timed about a center point for each of said one or more measurement periods.

2. An apparatus as recited in claim 1, wherein each modulation waveform is orthogonal to all other modulation waveforms, and each demodulation waveform is orthogonal to all other demodulation waveforms.

3. An apparatus as recited in claim 2, wherein each of said modulation waveforms and demodulation waveforms are of a type selected from a group consisting of:
   sinusoidal waveforms;
   square waveforms; and
   combinations of sinusoidal and square waveforms.

4. An apparatus as recited in claim 1, wherein said modulation waveforms each define a different exact integer number of cycles for each of said one or more measurement periods.

5. An apparatus as recited in claim 4, wherein said demodulation waveforms each define a different integer number of cycles that is equal to said different integer number of cycles defined by said modulation waveforms, respectively, for each of said one or more measurement periods.

6. An apparatus as recited in claim 1, further comprising:
   a sampling means for sampling a detector output signal to provide said composite signal, wherein said sampling means samples at a rate at least 2 times greater than a highest one of said different light source modulation frequencies.

7. An apparatus as recited in claim 6, wherein said demodulation means comprises:
   a processor for separately processing a first plurality of values and a second plurality of values comprising said first and second signal portions, respectively, for each of said one or more measurement periods, to determine said blood analyte level in said tissue under test.

8. A method for use in a photoplethysmographic measurement system comprising a plurality of pulsed light sources for illuminating a tissue under test and a detector for receiving at least a portion of the light pulses that is transmitted by the tissue under test and outputting a detector signal indicative of the intensity of the received portion of the light pulses, the method comprising:
   modulating each of the plurality of light sources according to a predefined plurality of different periodic modulation waveforms at a corresponding different one of a plurality of pulsing frequencies and in accordance with a predetermined phase relationship therebetween;
   demodulating a composite signal according to a predefined plurality of different periodic demodulation waveforms which correspond to said plurality of modulation waveforms, wherein said composite signal corresponds with said detector output signal based on said different pulsing frequencies and predetermined phase relationship, wherein the modulating and demodulating steps corresponding with each given one of said plurality of pulsing frequencies are synchronized so that each of said plurality of periodic modulation and demodulation waveforms are symmetrically timed about a center point of a blood analyte measurement period, and wherein demodulated signal portions corresponding with each of said plurality of light sources are obtained for said blood analyte measurement period.

9. A method as recited in claim 8, wherein said plurality of periodic modulation waveforms and demodulation waveforms completes an integer number of cycles during said measurement period.

10. A method as recited in claim 8, wherein each of said corresponding modulation and demodulation waveforms are orthogonal to all other modulation and demodulation waveforms comprising said plurality of periodic modulation waveforms and demodulation waveforms.

11. A method as recited in claim 8, further comprising:
    sampling said detector output signal at a predetermined rate to obtain said composite signal, wherein said composite signal comprises a series of measurement values for said measurement period, and wherein said predetermined rate is at least 2 times greater than a greatest one of said plurality of pulsing frequencies.

12. A method as recited in claim 11, further comprising:
    separately multiplying each of said series of measurement values by corresponding-in-time relative values extracted from each of said plurality of different periodic demodulating waveforms to obtain said demodulated signal portions; and
    separately summing said demodulated signal portions corresponding with each of said plurality of light sources for said measurement period to obtain a corresponding plurality of values which are each indicative of an intensity of said received portion of the light pulses corresponding with a different one of said plurality of pulsed light sources.

13. A method for determining a blood analyte level in tissue under test, the method comprising:
    emitting first and second light signals at different corresponding wavelengths into the tissue over at least one predetermined time period, wherein said first and second light signals are emitted according to first and second periodic modulation waveforms having first and second frequencies, wherein said first and second periodic modulation waveforms are timed to be symmetric about a center point of said time period;
    detecting said first and second light signals relative to said tissue and generating a composite signal indicative thereof;
    processing said composite signal using corresponding-in-time values from first and second periodic demodulation waveforms which correspond in phase and frequency with said first and second periodic modulation waveforms, respectively, to determine a first plurality of values and a second plurality of values corresponding to said first and second light signals applied to the tissue; and
    employing said first plurality of values and said second plurality of values to determine a blood analyte level in the tissue.

14. A method as recited in claim 13, wherein said periodic modulation waveforms and demodulation waveforms complete an integer number of cycles during said time period.

15. A method as recited in claim 13, wherein each of said corresponding first modulation and first demodulation waveforms are orthogonal to said second modulation and second demodulation waveforms.

* * * * *